(12) United States Patent
Fagan

(10) Patent No.: US 6,196,995 B1
(45) Date of Patent: Mar. 6, 2001

(54) REINFORCED EDGE EXCHANGE CATHETER

(75) Inventor: John R. Fagan, Pepperell, MA (US)

(73) Assignee: Medtronic AVE, Inc., Santa Rosa, CA (US)

( * ) Notice: Subject to any disclaimer, the term of this patent is extended or adjusted under 35 U.S.C. 154(b) by 0 days.

(21) Appl. No.: 09/164,009

(22) Filed: Sep. 30, 1998

(51) Int. Cl.$^7$ .................................................. A61M 29/00
(52) U.S. Cl. ...................... 604/96.01; 606/191; 604/161; 604/160
(58) Field of Search .............................. 604/96, 160, 161, 604/101, 102; 606/191–198; 600/433–435, 585

(56) References Cited

U.S. PATENT DOCUMENTS

| | | |
|---|---|---|
| 4,747,833 | 5/1988 | Kousai et al. . |
| 4,748,982 | 6/1988 | Horzewski et al. . |
| 4,776,846 | 10/1988 | Wells . |
| 4,988,356 * | 1/1991 | Crittenden et al. .................. 606/192 |
| 5,135,535 | 8/1992 | Kramer . |
| 5,154,725 | 10/1992 | Leopold . |
| 5,171,222 | 12/1992 | Euteneuer et al. . |
| 5,188,605 | 2/1993 | Sleep . |
| 5,195,978 | 3/1993 | Schiffer . |
| 5,205,822 | 4/1993 | Johnson et al. . |
| 5,219,332 * | 6/1993 | Nelson et al. ........................... 604/95 |
| 5,263,932 | 11/1993 | Jang . |
| 5,312,355 | 5/1994 | Lee . |
| 5,324,269 | 6/1994 | Miraki . |
| 5,334,147 | 8/1994 | Johnson . |
| 5,346,505 | 9/1994 | Leopold . |
| 5,389,087 | 2/1995 | Miraki . |
| 5,462,530 | 10/1995 | Jang . |

FOREIGN PATENT DOCUMENTS

| | | |
|---|---|---|
| 8-112352 | 5/1996 | (JP) . |
| WO 96/20750 | 7/1996 | (WO) . |

OTHER PUBLICATIONS

English language abstract for Japanese Patent No. 8112352 obtained from the Dialog Japio database.
English language abstract for Japanese Patent No. 8112352 obtained from the Derwent WPI database.

* cited by examiner

Primary Examiner—Glenn K. Dawson
Assistant Examiner—Catherine Serke
(74) Attorney, Agent, or Firm—Sterne, Kessler, Goldstein & Fox P.L.L.C.

(57) ABSTRACT

The invention relates to a catheter and guidewire exchange system in which the guidewire is contained within an indwelling portion of the catheter and with the guidewire and the catheter being separated externally of the patient. The catheter includes a guidewire lumen and a longitudinal slit which penetrates through the catheter wall and into the guidewire lumen. The catheter walls adjacent the slit are provided with reinforced edges which function to maintain the slit in a normally closed position during the catheterization procedure, when desired.

7 Claims, 2 Drawing Sheets

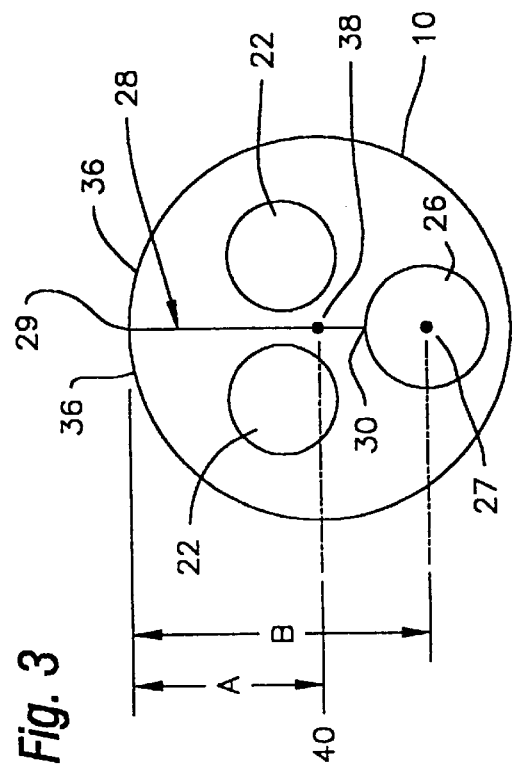
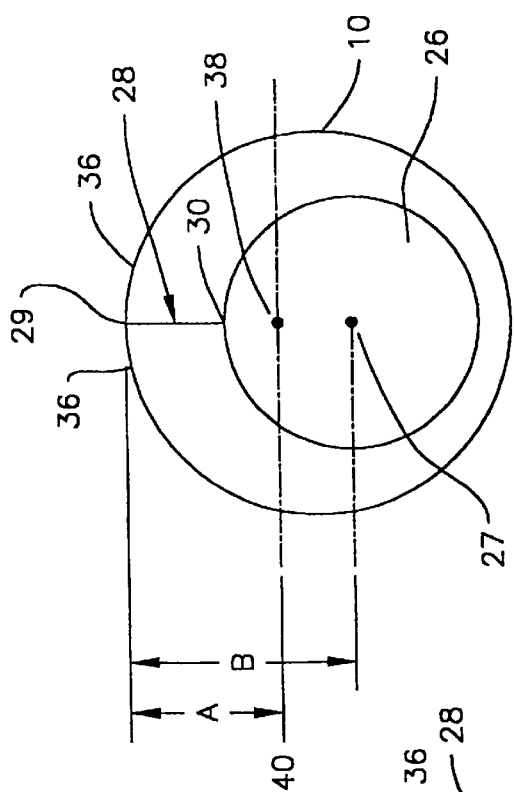
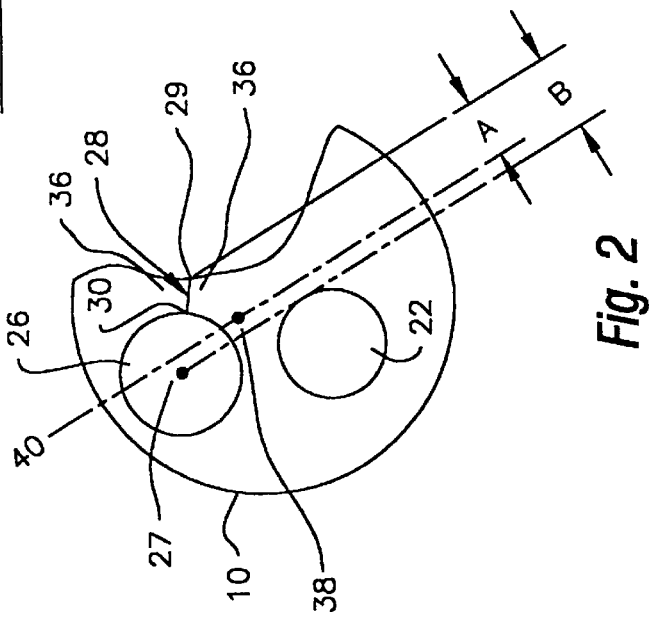

REINFORCED EDGE EXCHANGE CATHETER

FIELD OF INVENTION

The present invention relates in general to catheter systems employed in intravascular procedures. More particularly, the present invention relates to catheter systems for facilitating the exchange of catheters and/or guidewires, and for the transport of such catheters and/or guidewires to a selected site within the patient's vasculature without the need for guidewire extensions or exchange wires.

BACKGROUND OF THE INVENTION

Catheters are widely used by the medical profession for a variety of purposes and procedures. For example, catheters are commonly used in the treatment of atherosclerotic lesions or stenoses formed on the interior walls of the arteries. One procedure developed for the treatment of such lesions or stenoses is coronary angioplasty. The most commonly practiced angioplasty procedure is known as percutaneous transluminal coronary angioplasty, or PTCA. According to this procedure, a balloon located at the distal end of a dilatation catheter is guided through the patient's vasculature and positioned within the stenosis. The balloon is then inflated such that it dilates the stenosis and opens the restricted area of the artery. After a short period of time, the balloon is deflated and removed from the patient's vasculature.

Typically, the dilatation catheter is maneuvered through the patient's vasculature with the use of a flexible guidewire having a diameter of approximately 0.018 to 0.015 inches and a length of about 180 centimeters. The distal end of the guidewire is extremely flexible so that it may be routed through the convoluted arterial pathway to the site of the stenosis. After the distal portion of the guidewire is positioned across the stenosis, a dilatation catheter having a lumen adapted to receive the guidewire is advanced over the guidewire until the balloon is positioned within the stenosis.

During a catheterization procedure, it may be necessary to thread a catheter on or off an indwelling guidewire, or exchange an indwelling catheter with another catheter over an indwelling guidewire. When using a conventional over-the-wire catheter having a guidewire lumen extending throughout the length of the catheter, it is necessary to extend the guidewire outside the patient's body a sufficient distance to enable the catheter to be threaded on the guidewire without disturbing the position of the distal end of the guidewire within the stenosis. Because of the difficulty in managing such a long guidewire, the additional length of guidewire needed is typically provided through the use of a guidewire extension which is temporarily "linked" or attached to the proximal end of the guidewire. Once the catheter has been threaded onto the guidewire extension and advanced over the guidewire through the patient's vasculature, the guidewire extension may be detached from the guidewire.

Alternatively, an exchange wire on the order of 300 centimeters may be guided through the patient's vasculature such that its distal portion is positioned across the stenosis. The catheter may then be advanced over the exchange wire without disturbing the position of the distal end of the wire. After the balloon located at the distal end of the catheter is positioned within the stenosis, the exchange wire may be removed from the guidewire lumen and replaced with a shorter, easier to handle guidewire.

A number of alternative dilatation catheter designs have been developed in an attempt to eliminate the need to use guidewire extensions or exchange wires. One such catheter design is disclosed in U.S. Pat. No. 4,988,356 issued to Crittenden et al. This catheter and guidewire exchange system includes a catheter shaft having a slit which extends longitudinally between the proximal end and the distal end of the catheter and radially from the catheter shaft outside surface to the guidewire lumen. A guide member slidably coupled to the catheter shaft functions to open the slit such that the guidewire may extend transversely into or out of the slit at any location along the length of the slit. When using this system, the guidewire is maneuvered through the patient's vascular system such that the distal end of the guidewire is positioned across the treatment site. With the guide member positioned near the distal end of the catheter, the proximal end of the guidewire is threaded into the guidewire lumen opening at the distal end of the catheter and through the guide member such that the proximal end of the guidewire protrudes out the proximal end of the guide member. By securing the guide member and the proximal end of the guidewire in a fixed position, the catheter may then be transported over the guidewire by advancing the catheter toward the guide member. In doing so, the guide member slides down the length of the catheter and spreads the slit such that the guidewire lumen envelops the guidewire as the catheter is advanced into the patient's vasculature. The catheter may be advanced over the guidewire in this manner until the distal end of the catheter having the inflation balloon is positioned within the stenosis and essentially the entire length of the guidewire is encompassed within the guidewire lumen.

Furthermore, the indwelling catheter may be exchanged with another catheter by reversing the operation described above. To this end, the indwelling catheter may be removed by holding the proximal end of the guidewire and the guide member in a fixed position and withdrawing the proximal end of the catheter from the patient. When the catheter has been withdrawn to the point where the guide member has reached the distal end of the slit, the portion of the catheter over the guidewire is of a sufficiently short length that the catheter may pass over the proximal end of the guidewire without disturbing the position of the guidewire within the patient. After the catheter has been removed, another catheter fitted with a guide member and a longitudinal slit may be threaded onto the guidewire and advanced over the guidewire in the same manner described above with regard to the original catheter.

Another catheter design having a slitted catheter shaft in communication with a guidewire lumen is disclosed in U.S. Pat. No. 4,748,982 issued to Horzewski et al. This catheter design includes a guidewire lumen which extends along only a short portion of the distal end of the catheter. Accordingly, when the catheter is advanced over the guidewire, the guidewire is located outside the catheter except for the short segment which passes through the guidewire lumen at the distal end of the catheter. As disclosed in Horzewski et al., the catheter shaft defining the guidewire lumen includes a longitudinal slit which extends from the proximal end of the guidewire lumen toward the distal end of the guidewire lumen. This slit facilitates the exchange of catheters by shortening the length over which the guidewire extends through the guidewire lumen during removal of the catheter. When it is desired to exchange the indwelling catheter with another catheter, the catheter is withdrawn from the patient until the proximal end of the guidewire lumen extends outside the patient. From this point as the catheter is further withdrawn from the patient, the guidewire can be pulled out through the slit until the catheter has been withdrawn to the point of the termination of the slit near the distal end of the guidewire lumen. The portion of the catheter remaining over the guidewire is of sufficiently short length that it can be removed over the proximal end of the guidewire without disturbing the position of the distal end of the guidewire within the patient.

Despite these advantages slitted catheters have been known to fail to adequately contain the guidewire within the guidewire lumen during normal operation. More particularly, as the catheter is advanced over the guidewire through the patient's convoluted vasculature it is often bent such that the catheter slit buckles and creates an opening through which the guidewire may protrude. Should the guidewire protrude through the slit it may possibly cause trauma to the interior walls of the arteries. In addition, should the guidewire protrude from and subsequently become pinched within the slit, the distal end of the guidewire may be pulled out of or pushed beyond the treatment site, thus complicating the procedure and requiring repositioning within the patient's vasculature.

SUMMARY OF THE INVENTION

It is, therefore, a principal object of the present invention to provide an improved catheter and guidewire system.

It is a further object of the present invention to provide an improved catheter and guidewire system having a reinforced catheter slit which opens to allow transport of the catheter within a patient's vasculature over a guidewire or removal of an indwelling catheter without effecting the position of the guidewire within the patient's vasculature.

It is a further object of the present invention to provide an improved catheter and guidewire system having a reinforced catheter slit which remains closed to contain the guidewire within the guidewire lumen, when desired.

It is also an object of the present invention to provide an improved catheter and guidewire system having a reinforced catheter slit which enables catheter exchanges without the use of extension guidewires or long exchange guidewires.

It is a further object of the present invention to provide an improved catheter and guidewire system having a reinforced catheter slit which enables guidewire exchanges through the catheter guidewire lumen.

Objects and advantages of the invention are set forth in part above and in part below. In addition, these and other objects and advantages of the invention will become apparent herefrom, or may be appreciated by practice with the invention, the same being realized and attained by means of instrumentalities, combinations and methods pointed out in the appended claims. Accordingly, the present invention resides in the novel parts, constructions, arrangements, improvements, methods and steps herein shown and described.

BRIEF DESCRIPTION OF THE DRAWINGS

The invention will be further described, by way of example, with reference to the accompanying drawings, wherein:

FIG. 2 is a cross-sectional view of the catheter tube of the present invention taken along line 2—2 of FIG. 1;

FIG. 3 is a cross-sectional view of a second embodiment of the catheter shaft of the present invention; and FIG. 4 is a cross-sectional view of a third embodiment of the catheter shaft of the present invention.

DESCRIPTION OF THE PREFERRED EMBODIMENTS

Figure 1:
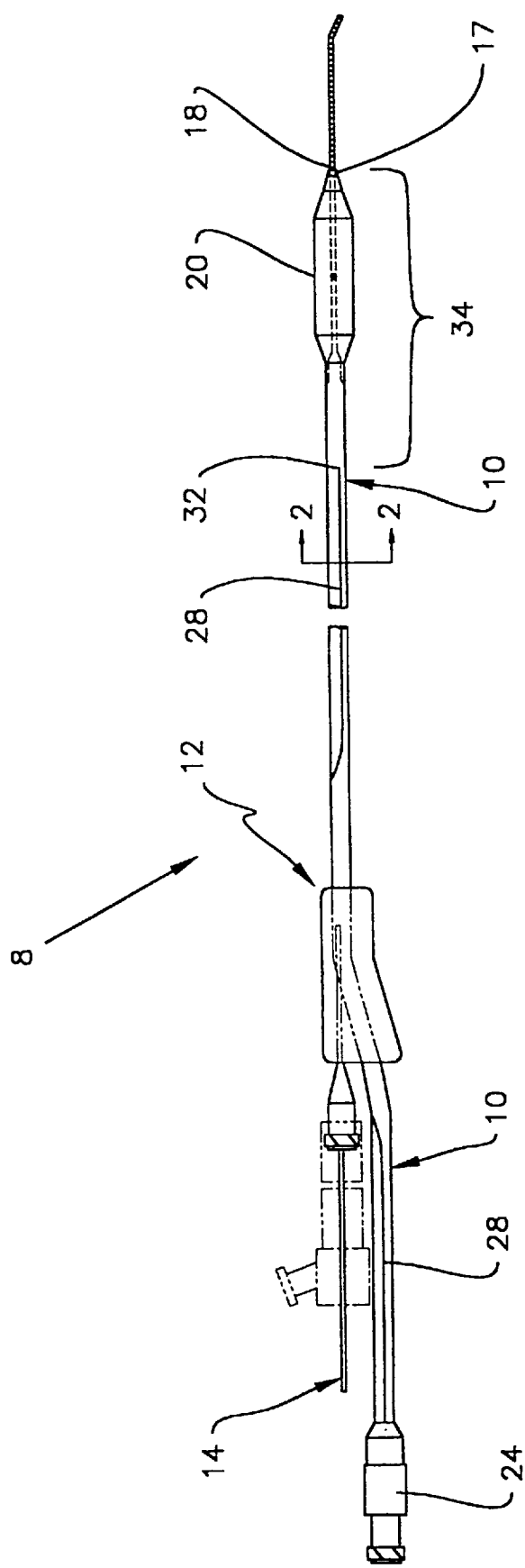
FIG. 1 is a schematic drawing showing a plan view of a balloon catheter employing the reinforced edge catheter shaft according to the present invention.

It should be noted that while the following description will be specifically in the context of coronary angioplasty dilatation catheters, the invention is not so limited and is applicable to other catheter assemblies and procedures. For example, it will be understood that the present invention also applies to drug delivery and/or stent delivery catheters.

Referring generally to the embodiments of the invention shown in the accompanying drawings, wherein like reference numbers refer to like parts throughout the various views, the basic principles of the broadest aspects of the invention can be appreciated from FIGS. 1 and 2.

The basic principles of the present invention will be described with reference to the preferred embodiment of the balloon dilatation catheter disclosed in U.S. Pat. No. 4,988, 356 issued to Crittenden et al. To this end, the Crittenden et al. patent is incorporated herein by reference in its entirety.

As shown in FIG. 1, a dilatation catheter, indicated generally as 8, embodying the present invention comprises an elongated, flexible catheter shaft 10 having two inner lumens extending longitudinally between the proximal and distal ends of the catheter shaft. The catheter includes an inflation balloon 20 located at the distal end of the catheter shaft 10. A guide member 12 is slidably received over catheter shaft 10 and functions to merge or separate catheter shaft 10 and guidewire 14. The proximal end of catheter shaft 10 further includes a fitting 24 which is designed to be coupled to a suitable source of pressurized fluid for inflating or a suction device for deflating balloon 20.

Referring now to FIGS. 1 and 2, inflation lumen 22 is adapted to provide flow communication between fitting 24 and the interior of balloon 20. Guidewire lumen 26 is adapted to slidably receive a guidewire 14. Guidewire lumen 26 may extend the full length of catheter shaft 10, terminating at the distal outlet 18. The cross-section of guidewire lumen 26 may comprise any general configuration, however, it should be dimensioned to be greater than the cross-section of guidewire 14 to permit relative longitudinal movement between guidewire 14 and catheter shaft 10.

In accordance with the present invention, catheter shaft 10 includes a slit 28 extending longitudinally between the distal end and the proximal end of the catheter shaft. The proximal end of slit 28 may terminate at or near fitting 24. In the embodiment shown in FIG. 1, in which the catheter includes a balloon 20 at its distal end, the distal end 32 of slit 28 terminates short of the distal tip 17 of the catheter shaft, thereby leaving a distal segment 34 of the catheter shaft which is unslit and in which the guidewire lumen 26 is defined by a continuous surrounding wall. It should be understood, however, that the principles of the present invention are usable with catheters which do not have a balloon or other encircling members at the distal end of the catheter shaft. Accordingly, the present invention may be usable with catheters having a slit 28 which extends fully to the distal tip of the catheter shaft.

With reference to the two-lumen catheter shaft embodiment shown in FIG. 2, slit 28 extends from a first end 29 through the catheter tube wall to a second end 30. Slit 28 may be considered as defining a pair of flaps 36 which are normally closed to form an enclosed guidewire lumen 26. As illustrated in FIG. 2, the cross-section of catheter shaft 10 defines a centroid 38 through which a principal axis 40 passes. The principal axis 40 is defined as the line passing through centroid 38 with respect to which the second moment of inertia for the catheter cross-sectional area is a minimum. As further illustrated in FIG. 2, the cross-section of guidewire lumen 26 defines a center point 27. According to the present invention, guidewire lumen 26 is disposed within the catheter shaft 10 such that the closing force of flaps 36 exceeds the buckling forces which may be exerted on the catheter shaft when the catheter is routed through the patient's vasculature. The maximum cross-sectional diameter of catheter shaft 10 is a finite measure so that it may fit through a patients vasculature. To provide the desired forces for maintaining the flaps 36 in their closed position, guidewire lumen 26 is disposed within the as catheter shaft such that the distance between the principal axis 40 of the catheter cross-section and the slit first end 29 (designated as A) is less than the distance between the guidewire lumen center point 27 and the slit first end 29 (designated as B).

As shown in FIG. 3, the present invention can be applied to a catheter having a single lumen catheter shaft 10. In this embodiment, catheter shaft 10 includes a guidewire lumen 26 and a slit 28. Slit 28 extends longitudinally from the proximal end toward the distal end of the catheter shaft and radially through the catheter shaft wall from a first end 29 to a second end 30. As here embodied, the guidewire lumen 26 is disposed within the catheter shaft 10 such that the distance between the principal axis 40 of the catheter cross section and the slit first end 29 (designated as A) is less than the distance between the guidewire lumen center point 27 and the slit first end 29 (designated as B).

By further example, the present invention can also be adapted for use with a catheter having a three lumen catheter shaft. As illustrated in FIG. 4, catheter shaft 10 includes two inflation lumens 22 and a guidewire lumen 26. Catheter shaft 10 further includes a slit 28 which extends longitudinally from the proximal end toward the distal end of the catheter and radially through the catheter wall from a first end 29 to a second end 30. Again as provided by the present invention, guidewire lumen 26 is disposed within catheter shaft 10 such that the distance between the principal axis 40 of the catheter cross section and the slit first end 29 (designated as A) is less than the distance between the guidewire lumen center point 27 and the slit first end 29 (designated as B).

It should be understood that although the invention is described, for purposes of illustration, as being used in connection with a balloon catheter of the type disclosed in U.S. Pat. No. 4,988,356 issued to Crittenden, the invention is not limited to practice with that type of catheter. The invention may be practiced with any type of catheter having a slitted catheter shaft. For example, the reinforced edge of the present invention may be used with the slitted catheter disclosed in U.S. Pat. No. 4,748,982 issued to Horzewski et al.

While only a few embodiments have been illustrated and described in connection with the present invention, various modifications and changes in both the apparatus and method will become apparent to those skilled in the art. All such modifications or changes falling within the scope of the claims are intended to be included therein.

I claim:

1. A catheter comprising, an elongated catheter body having a proximal end, a distal end, an outside surface, a lumen extending longitudinally through at least part of the catheter body, and a longitudinal slit formed in the catheter body and extending radially from a first end at the catheter body outside surface to the lumen, the catheter body having a cross-sectional area defining a centroid through which a principal axis passes, the lumen having a cross-sectional area defining a center point, the lumen being disposed within the catheter body such that the distance between the principal axis of the catheter body and the slit first end is less than the distance between the lumen center point and the slit first end.

2. The catheter according to claim 1, wherein the lumen and slit extend essentially the entire length of the catheter body.

3. The catheter according to claim 2, wherein the lumen is adapted to receive a guidewire therethrough.

4. The catheter according to claim 1, wherein the slit terminates proximal of the distal end of the catheter body thereby forming an unslit distal segment of the catheter.

5. The catheter according to claim 4 further comprising an encircling member coupled to the catheter on the unslit distal segment.

6. The catheter according to claim 5, wherein the encircling member is an inflatable balloon.

7. The catheter according to claim 6 further comprising a second lumen extending longitudinally through the catheter body having a proximal end adapted to be in flow communication with a source of pressurized fluid and a distal end in flow communication with the interior of the balloon for inflation and deflation of the balloon.

* * * * *